US008672853B2

(12) United States Patent  (10) Patent No.: US 8,672,853 B2
Young  (45) Date of Patent: Mar. 18, 2014

(54) PRESSURE SENSOR FOR MONITORING A SUBJECT AND PRESSURE SENSOR WITH INFLATABLE BLADDER

(75) Inventor: Steven J. Young, Los Gatos, CA (US)

(73) Assignee: BAM Labs, Inc., Campbell, CA (US)

( * ) Notice: Subject to any disclaimer, the term of this patent is extended or adjusted under 35 U.S.C. 154(b) by 543 days.

(21) Appl. No.: 12/815,653

(22) Filed: Jun. 15, 2010

(65) Prior Publication Data

US 2011/0306844 A1  Dec. 15, 2011

(51) Int. Cl.
*A61B 5/0205* (2006.01)

(52) U.S. Cl.
USPC ........... 600/483; 600/300; 600/301; 600/484; 600/529; 600/534

(58) Field of Classification Search
USPC ................. 600/301, 484, 529, 534, 300
See application file for complete search history.

(56) References Cited

U.S. PATENT DOCUMENTS

| 4,146,885 | A | | 3/1979 | Lawson, Jr. | |
|---|---|---|---|---|---|
| 4,387,722 | A | | 6/1983 | Kearns | |
| 4,657,025 | A | | 4/1987 | Orlando | |
| 4,862,144 | A | * | 8/1989 | Tao | 340/573.1 |
| 4,884,578 | A | | 12/1989 | Morgenstern | |
| 5,067,494 | A | | 11/1991 | Rienmueller et al. | |
| 5,271,055 | A | | 12/1993 | Hsieh et al. | |
| 5,351,550 | A | | 10/1994 | Maurer | |
| 5,485,833 | A | | 1/1996 | Dietz | |
| 5,501,231 | A | * | 3/1996 | Kaish | 600/538 |
| 5,515,865 | A | | 5/1996 | Scanlon | |
| 5,538,494 | A | | 7/1996 | Matsuda | |
| 5,552,205 | A | * | 9/1996 | Lea | 428/74 |
| 5,581,038 | A | | 12/1996 | Lampropoulos et al. | |
| 5,684,460 | A | | 11/1997 | Scanlon | |
| 5,796,340 | A | | 8/1998 | Miller | |
| 5,902,248 | A | * | 5/1999 | Millar et al. | 600/485 |
| 5,954,214 | A | * | 9/1999 | Guezennec et al. | 215/262 |

(Continued)

FOREIGN PATENT DOCUMENTS

JP  2001145605 A  5/2001
JP  2004-049838 A  2/2004

(Continued)

OTHER PUBLICATIONS

Notification of Transmittal, International Search Report and Written Opinion of the International Searching Authority dated Dec. 29, 2011 from the corresponding International Patent Application No. PCT/US2011/039744 filed Jun. 9, 2011.

(Continued)

*Primary Examiner* — Patricia Mallari
*Assistant Examiner* — Puya Agahi
(74) *Attorney, Agent, or Firm* — Young Basile

(57) ABSTRACT

Pressure sensing devices for use with an inflatable bladder and monitoring apparatus for an at rest subject are disclosed herein. The device can comprise a housing comprising a recess and configured to be welded in a seam of the inflatable bladder. A pressure sensor can be located within the recess with a sensing side configured to be exposed to the cavity of the inflatable bladder and a reference side configured to be exposed to ambient air. A printed circuit board can be located within the recess and coupled to the pressure sensor. The pressure sensor is operable to detect a pressure change within the cavity due to a force exerted by a subject on the inflatable bladder.

18 Claims, 7 Drawing Sheets

(56) References Cited

U.S. PATENT DOCUMENTS

| | | | |
|---|---|---|---|
| 6,212,718 B1* | 4/2001 | Stolpmann et al. | 5/713 |
| 6,298,260 B1 | 10/2001 | Sontag et al. | |
| 6,375,621 B1 | 4/2002 | Sullivan | |
| 6,468,234 B1 | 10/2002 | Van der Loos et al. | |
| 6,491,647 B1 | 12/2002 | Bridger et al. | |
| 6,547,743 B2 | 4/2003 | Brydon | |
| 6,553,242 B1 | 4/2003 | Sarussi | |
| 6,633,775 B1 | 10/2003 | Bernard | |
| 6,719,708 B1 | 4/2004 | Jansen | |
| 6,731,970 B2 | 5/2004 | Schlossbauer et al. | |
| 6,764,451 B2 | 7/2004 | Holland et al. | |
| 6,849,049 B2* | 2/2005 | Starr et al. | 600/538 |
| 6,878,121 B2 | 4/2005 | Krausman et al. | |
| 6,898,456 B2 | 5/2005 | Erbel | |
| 6,984,207 B1 | 1/2006 | Sullivan et al. | |
| 7,048,697 B1 | 5/2006 | Mitsuru | |
| 7,678,063 B2* | 3/2010 | Felmlee et al. | 600/534 |
| 2002/0058875 A1* | 5/2002 | Doten et al. | 600/484 |
| 2003/0004427 A1* | 1/2003 | Swisa | 600/539 |
| 2004/0111045 A1 | 6/2004 | Sullivan et al. | |
| 2004/0245036 A1 | 12/2004 | Fujita et al. | |
| 2005/0043652 A1 | 2/2005 | Lovett et al. | |
| 2005/0177051 A1 | 8/2005 | Almen | |
| 2007/0125380 A1* | 6/2007 | Acker et al. | 128/204.23 |
| 2007/0149883 A1* | 6/2007 | Yesha | 600/485 |
| 2008/0077020 A1* | 3/2008 | Young et al. | 600/484 |
| 2008/0167561 A1* | 7/2008 | Ruotoistenmaki | 600/484 |
| 2009/0082700 A1* | 3/2009 | Whalen et al. | 600/595 |
| 2009/0183312 A1* | 7/2009 | Price et al. | 5/706 |
| 2009/0192364 A1* | 7/2009 | Voto et al. | 600/301 |
| 2010/0036266 A1* | 2/2010 | Myklebust et al. | 600/500 |
| 2010/0113890 A1* | 5/2010 | Cho et al. | 600/301 |
| 2010/0144063 A1* | 6/2010 | Furumiya et al. | 438/3 |
| 2010/0170043 A1* | 7/2010 | Young et al. | 5/706 |
| 2010/0174198 A1* | 7/2010 | Young et al. | 600/484 |
| 2010/0174199 A1* | 7/2010 | Young et al. | 600/484 |
| 2010/0280446 A1* | 11/2010 | Kalpin | 604/67 |
| 2010/0298723 A1* | 11/2010 | Zhen | 600/490 |

FOREIGN PATENT DOCUMENTS

| | | |
|---|---|---|
| JP | 2004-113618 A | 4/2004 |
| JP | 2004-130012 A | 4/2004 |
| JP | 2007-125337 A | 5/2007 |
| JP | 2008-259745 A | 10/2008 |
| JP | 2010-094379 A | 4/2010 |
| WO | 2004 045407 A1 | 6/2004 |
| WO | 2005 079530 A2 | 9/2005 |

OTHER PUBLICATIONS

EPO Communication dated Dec. 5, 2013 with Extended EP Search Report which includes the Supplementary EP Search Report and the EP Search Opinion from the corresponding European Patent Application No. 11796203.5-1657 filed Jun. 9, 2011.

* cited by examiner

US 8,672,853 B2

PRESSURE SENSOR FOR MONITORING A SUBJECT AND PRESSURE SENSOR WITH INFLATABLE BLADDER

FIELD OF THE INVENTION

The present invention pertains to an inflatable bladder having a pressure sensor for use in monitoring vital signs, such as the presence of a person and their heartbeat and breathing rates, in an human or animal, e.g., an infant sleeping in a crib, a patient in a hospital setting, a person with a chronic disease, a person in an elder-care setting, or an animal at home or in the care of a professional, and a pressure sensor device for use with an inflatable bladder.

BACKGROUND

Historically, monitoring vital signs of a person has required expensive equipment, such as an electrocardiogram (EKG) or a ballistocardiograph (BCG). In addition to being prohibitively expensive for many situations (e.g., home use), both EKGs and BCGs can be too cumbersome for use outside of medical facilities. EKGs, for example, typically necessitate attaching electrodes to the bodies of users, while BCGs rely on large, heavy, and unaesthetic force-measuring platforms that users lie on.

In more recent times, devices including piezoelectric films or arrays of sensors have been developed to measure heart and respiration rates. A user can lie on the device, and the film or sensors can generate a signal indicative of the user's heart rate and/or respiration rate. However, these devices can also be expensive. Existing devices on which a user can lie for comfort already exist. Utilizing existing components increasing manufacturing efficiency and reduces cost.

SUMMARY

Disclosed herein are embodiments of an apparatus for monitoring a subject at rest. One embodiment of an apparatus for monitoring a subject at rest comprises an inflatable bladder having a cavity comprising a fluid and a housing comprising a recess and hermetically sealed within a seam of the inflatable bladder. Within the housing is a pressure sensor located within the recess, the pressure sensor having a sensing side exposed to the cavity of the inflatable bladder and a reference side exposed to ambient air and a printed circuit board located within the recess and coupled to with the pressure sensor, wherein the pressure sensor is operable to detect a pressure change within the cavity due to a force exerted by a subject on the inflatable bladder.

Also disclosed herein are embodiments of pressure sensing device for use with an inflatable bladder. One embodiment disclosed herein comprises a housing comprising a recess and configured to be welded in a seam of the inflatable bladder. A pressure sensor is located within the recess, the pressure sensor having a sensing side configured to be exposed to the cavity of the inflatable bladder and a reference side configured to be exposed to ambient air. A printed circuit board is located within the recess in communication with the pressure sensor. The pressure sensor is operable to detect a pressure change within the cavity due to a force exerted by a subject on the inflatable bladder.

BRIEF DESCRIPTION OF THE DRAWINGS

The description herein makes reference to the accompanying drawings, wherein like reference numerals refer to like parts throughout the several views, and wherein.

DETAILED DESCRIPTION

A pressure sensor apparatus is provided for monitoring the presence and health status of human and animal subjects/patients. The apparatus utilizes an inflatable air mattress, bladder or pad adapted to the placed between a subject and a support substrate, such as a bed, cushion, infant crib, chair or the like. Welded in place at the corner or edge of the bladder is an inflation valve used to provide an air nozzle through which fluid is pumped. In accordance with the invention, a housing that is sized and configured in substantially the same dimensions as the inflation valve is provided to hold a pressure sensor module, which monitors the pressure changes in the pad in response to a subject's heart function or respiration. The new housing is sized and configured substantially identical to the old housing so that tooling and equipment used to assemble the mattress can be used with minimal modification to insert and weld into place the new housing.

Figure 1:
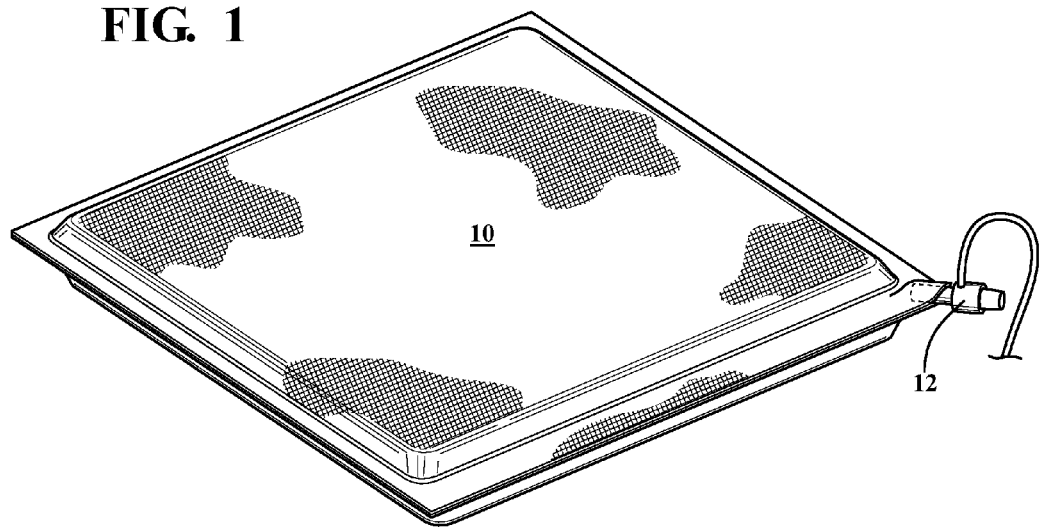
FIG. 1 is a perspective view of an embodiment of an apparatus for measuring a subject at rest as disclosed herein.

As shown in FIG. 1, an inflatable mattress or fluid bladder 10 is operably connected to a pump (not shown) or inflated by the presence of foam for filling a cavity within the fluid bladder 10 to a preselected pressure with a gas or liquid through inflation valve 12. The pump can be a rotary type pump or another type of pump. The pump can be fluidly coupled to the bladder 10 via a hose, or the pump can be coupled directly to the inflation valve 12 and be electrically driven as shown. The pump inflates the bladder 10 through inflation valve 12 located in a corner or an edge of the bladder 10. The pump can be disconnected from the inflation valve 12 with the inflation valve configured to maintain the air pressure within the bladder when the bladder is sufficiently filled with fluid.

To incorporate a monitoring system for a subject at rest into such an existing bladder, an assembly as shown in the remaining figures has been developed. The assembly has a housing 14 (shown in FIG. 2) that is substantially the same size and shape as the inflation valve 12 so that the same tooling can be used and the same sealing process can be used in order to incorporate the monitoring device.

Figure 2:
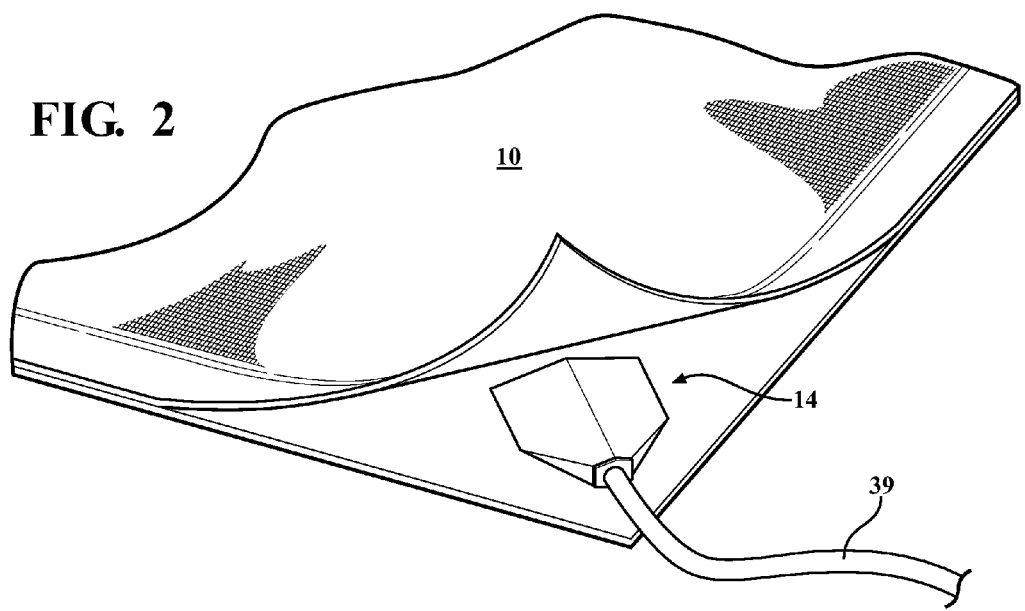
FIG. 2 is an exploded view of a portion of FIG. 1.
Figure 3:
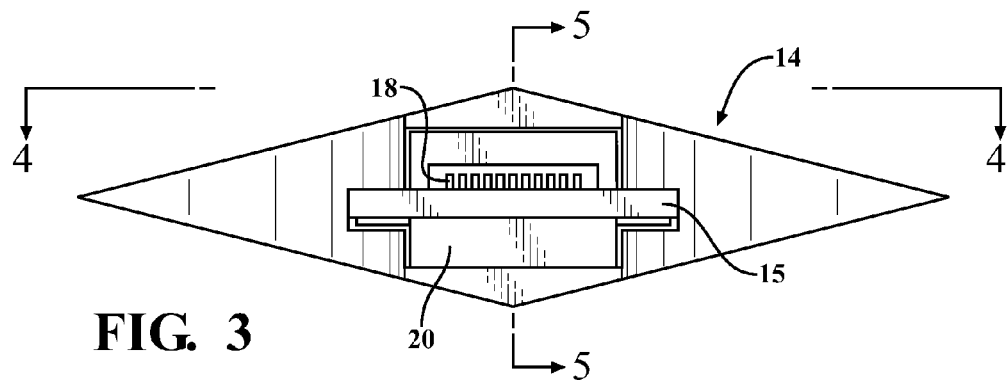
FIG. 3 is a cross sectional view of a pressure sensing device shown in FIG. 2 along line A.
Figure 5:
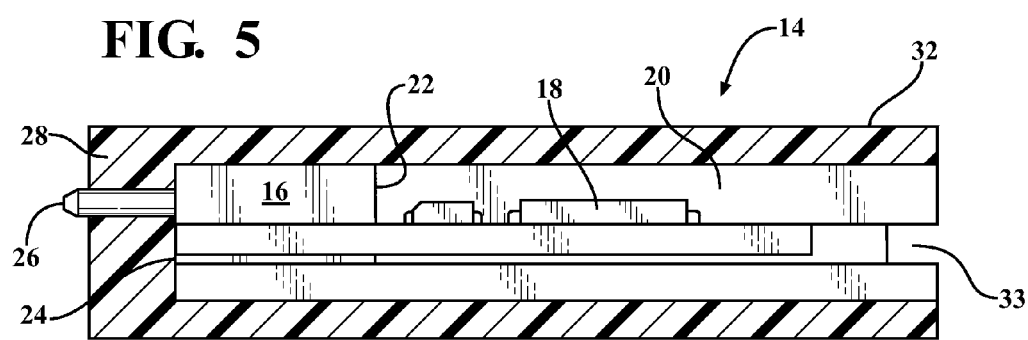
FIG. 5 is a cross sectional side view of the embodiment in FIG. 3 along line B.
Figure 4A:
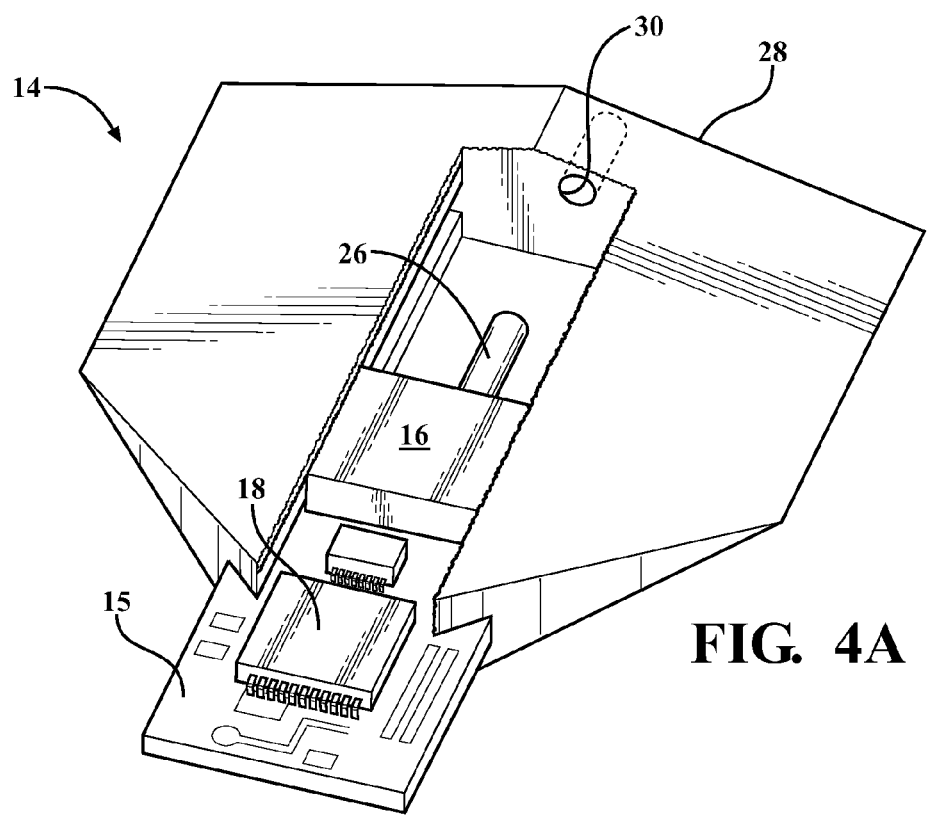
FIG. 4A is a cross sectional expanded view of FIG. 3 along line A.
Figure 4B:
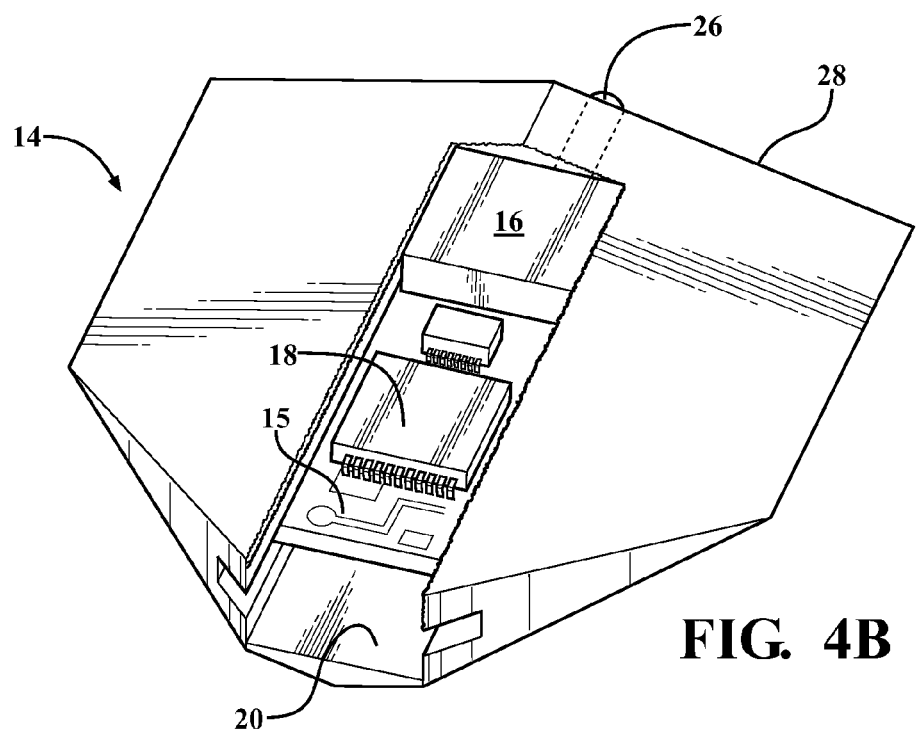
FIG. 4B is a cross sectional view of FIG. 3 along line A.

FIG. 2 is a perspective view of the housing 14 of the monitoring assembly and a corner of the fluid bladder 10. As seen in FIGS. 3-5, the housing 14 has a pressure sensor module 15 comprising a pressure sensor 16 connected to a printed circuit board (PCB) 18, which generates electrical signals in response to the pressure sensor 16 output. The housing 14 accepts the pressure module 15 in a tracked recess 20 within the housing 14. The pressure sensor 16 is at the distal end of the tracked recess 20 and positioned between the distal end and the PCB 18. The pressure sensor 16 has two sides. The reference side 22 is exposed to ambient air, while the sensing side 24 is exposed to the fluid within the cavity of the bladder 10. The pressure sensor 16 includes a stem 26 through which the sensing side 24 of the pressure sensor 16 is exposed to the fluid within the bladder 10.

Figure 6:
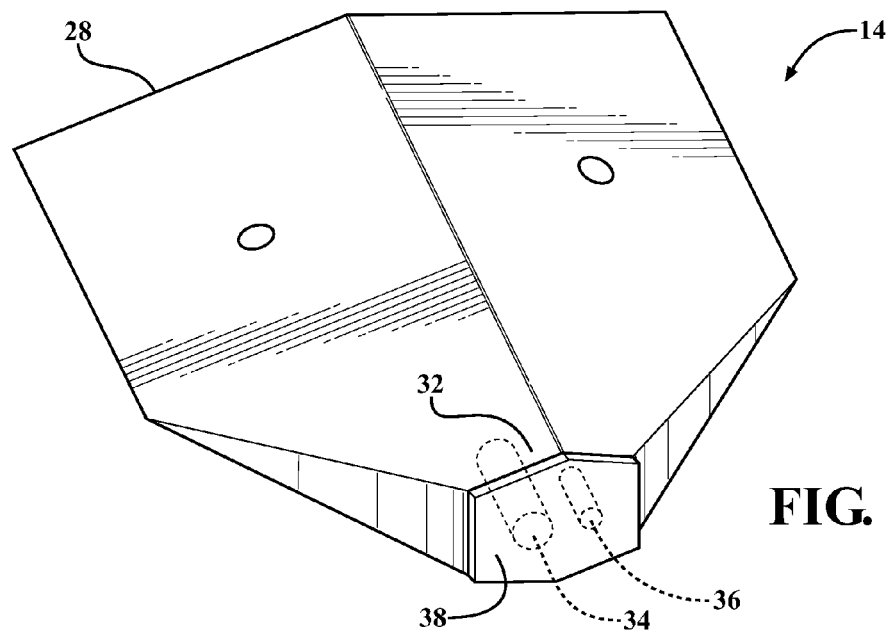
FIG. 6 is a perspective view of an embodiment of the pressure sensing device disclosed herein.

The pressure sensor 16 and the printed circuit board 18 are mounted on a planar base configured to slide within each track through the opening into the recess 20 so that the pressure sensor and printed circuit board are fully within the recess 20. The distal end 28 of the housing includes a tubular aperture 30 (shown in FIG. 4A) that is sized so that the stem 26 can snugly fit through the aperture 30. The proximal end 32 of the housing 14 is open to permit insertion of the pressure sensing module 15. The opening 33 at the proximal end 32 of the tracked recess 20 is sized to accommodate a plug 34 which can be made of flexible material. The plug 34 when inserted into the opening 33 of the proximal end 32 of the housing 14 seals the pressure sensor module 15 within the housing 14. The plug 34 can be seen inserted in FIG. 6. The flexible plug 34 includes two apertures: a first aperture 36 can provide a conduit for ambient air so that the reference side 22 of the pressure sensor 16 is exposed to ambient air. The second aperture 38 can be sized to snugly fit a wire providing electrical conduit between the PCB 18 and a device external to the mattress 10. FIG. 2 illustrates the conduit 39.

Figure 7:
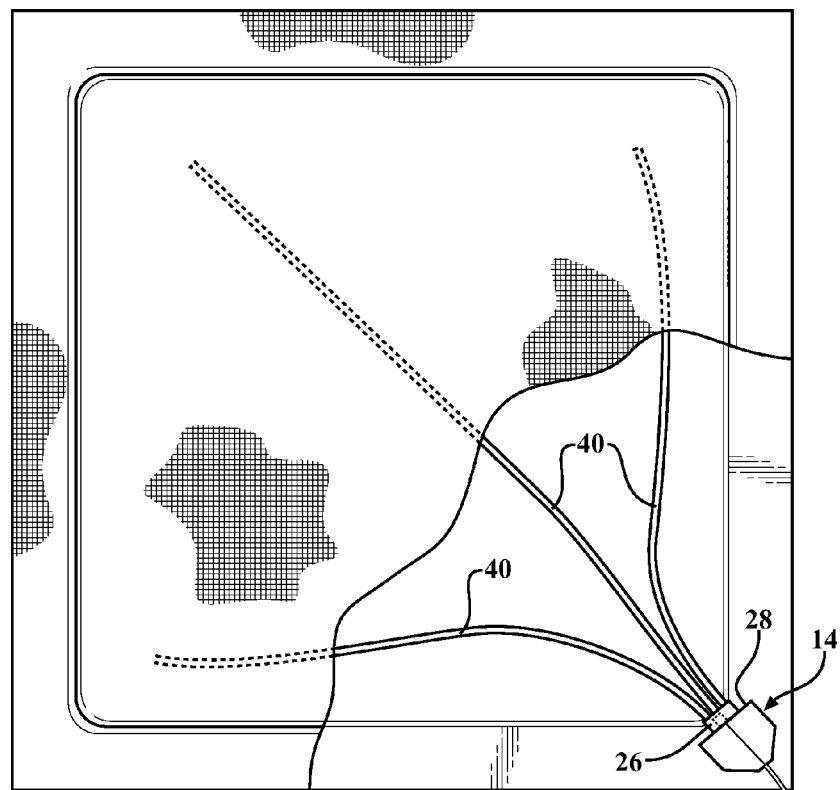
FIG. 7 is a plan view of another embodiment of a pressure sensing device disclosed herein.

As shown in FIG. 7, the tubular aperture 30 of the housing 14 can be connected to a plurality of tubes 40 of one or more lengths terminating in different locations within the bladder 10. The plurality of tubes 40 permits sampling of pressure in different locations throughout the bladder 10 while only requiring one pressure sensor module 15. Alternatively or in combination with, more than one housing 14 can be welded at different locations in the seam of the bladder 10.

Figure 8:
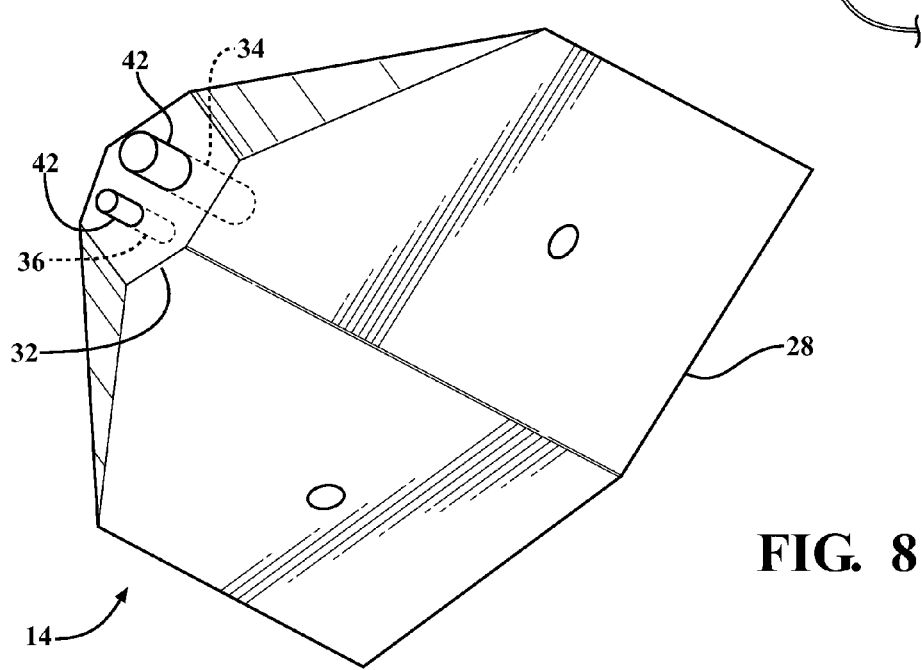
FIG. 8 is a perspective view of the pressure sensing device with a frangible cap.

The apertures 36, 34 on the plug 38 are sealed with a frangible cap 42, shown in FIG. 8. The cap 42 can be a single cap sealing both the first and second apertures 36, 34, or the cap 42 can be two distinct caps each sealing one of the first and the second apertures 36, 34. The frangible cap(s) 42 remains on during manufacture of the mattress 10 so that the housing 14 and pressure sensor module 15 can be subjected to a dunk test to confirm that a hermetic seal has been formed between the housing 14 and the bladder 10 and between the tubular aperture 30 on the distal end 28 of the housing 14 and the stem 26. After the dunk test, the frangible cap(s) 42 is removed to permit operation of the device.

Figure 9:
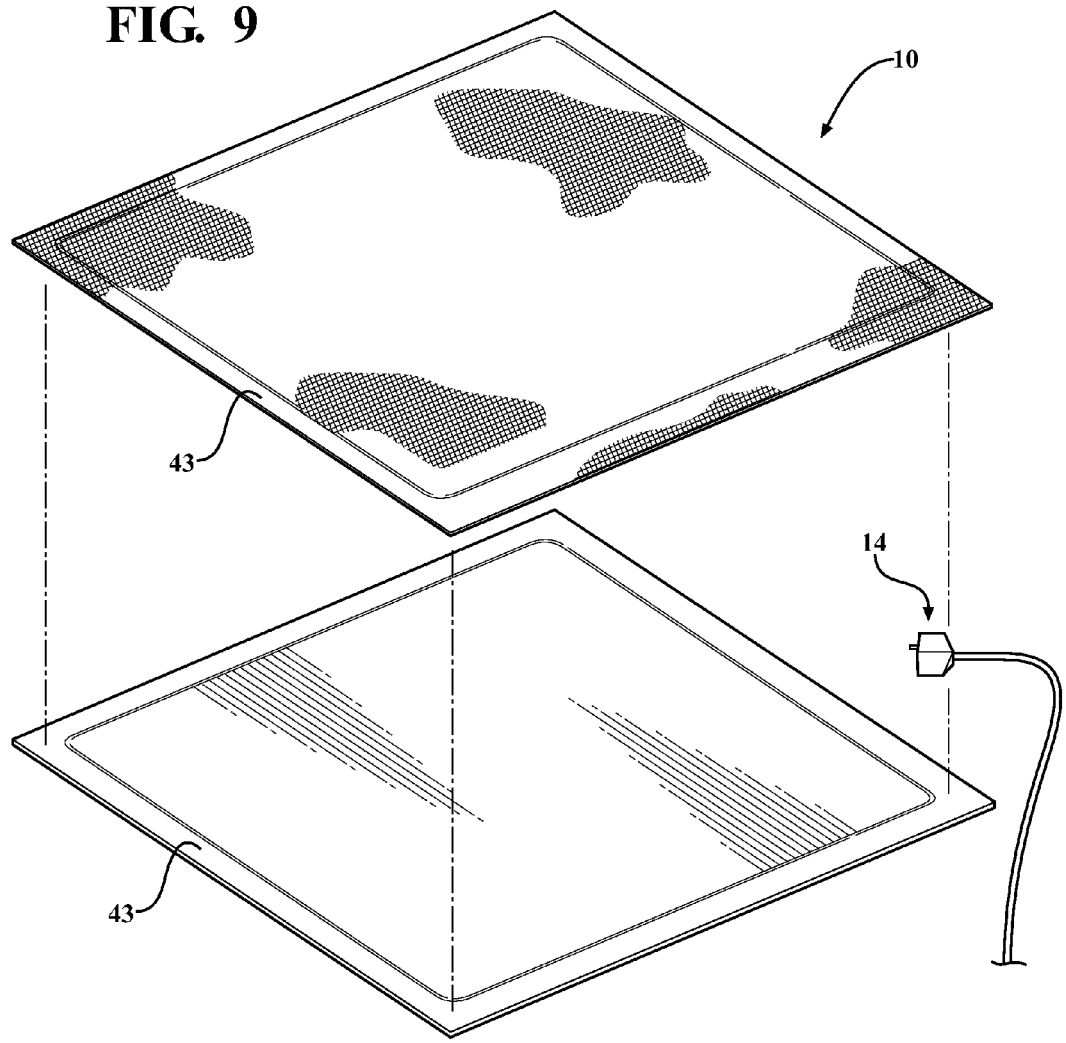
FIG. 9 is an exploded side view of an apparatus for measuring a subject at rest.

The fluid bladder 10 can be inflated with air or another fluid, such as water, gel, another gas, or a combination thereof. For example, compressed gas (e.g., compressed air or $CO_2$) can be used to inflate the bladder 10. The bladder is inflated as described earlier. It is also contemplated that the housing 14 of the monitoring assembly can be configured with a valve through which to inflate the bladder. As illustrated in FIG. 9, the fluid bladder 10 can comprise two shells 43 that are sealed along their periphery. The shells may be made of virtually any conventional material that is air or water-tight. Exemplary materials include but are not limited to plastic (e.g., polyethylene, polypropylene, latex, vinyl, etc.) and fabric (e.g., canvas). Fabrics may be treated with a plastic or other coating to make them air or fluid-tight, as required. The bladder 10 may be covered for comfort or protection, so long as the covering does not substantially insulate the cavity of the bladder 10 from the vibrations generated by the subjects heart and/or lung function.

Plastic shells may be hermetically sealed with ultrasonic welding as a non-limiting example. Other means of sealing the bladder 10 and the housing 14 known to those skilled in the art may be used. When the shells are welded, the tubular aperture 30 in the distal end 28 of the housing 14 melts, providing a hermetic seal so that fluid within the cavity of the mattress 10 is exposed to the sensing side 24 of the pressure sensor 16 through the stem 26.

Figure 10:
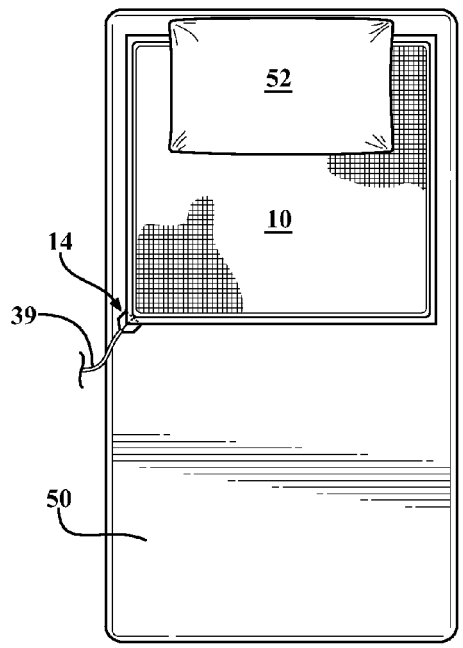
FIG. 10 is a plan view of another embodiment of an apparatus for measuring a subject at rest as disclosed herein.
Figure 11A:
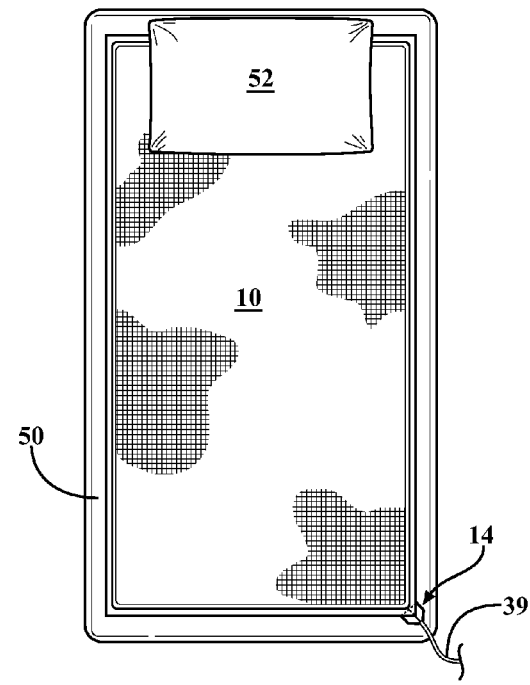
FIG. 11A is a plan view of another embodiment of an apparatus for measuring a subject at rest as disclosed herein.

The bladder 10 can cover a smaller area of the substrate 50. For example, in FIG. 10, a mattress is the substrate 50 shown with a pillow 52, with the bladder 10 sized to accommodate an area on which the torso of a subject is expected to be positioned. As noted, the substrate 50 can be a mattress, crib, cot, hospital bed, home bed, chair and the like. Alternatively, the bladder 10 can be sized to extend over a large portion of the substrate 50 upon which the subject is to lay, as shown in FIG. 11A. For example, the bladder 10 may be sized similar to a mattress 50. Thus, the size of the fluid bladder 10 can allow the fluid bladder 10 to sense pressure changes over a wide range of positions of the subject on the substrate. That is, even if the pressure sensor 16 is far from a source of a pressure change (e.g., a beating heart or inhaling or exhaling lungs of the subject), the pressure change can create a wave within the bladder 10 propagating the pressure change to the sensor 16. As noted above, the bladder 10 may contain a plurality of housings 14 around its perimeter. For example, a housing 14 may be welded into each corner of the bladder 10.

Figure 11B:
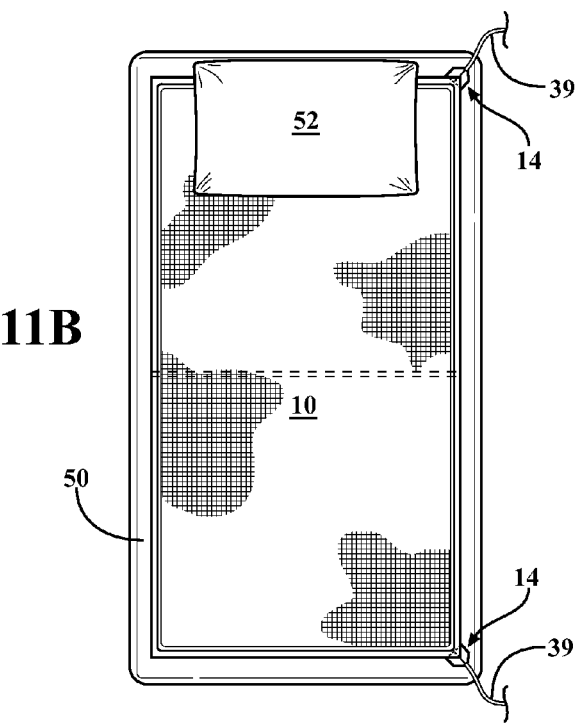
FIG. 11B is a plan view of another embodiment of an apparatus for measuring a subject at rest as disclosed herein.
Figure 12:
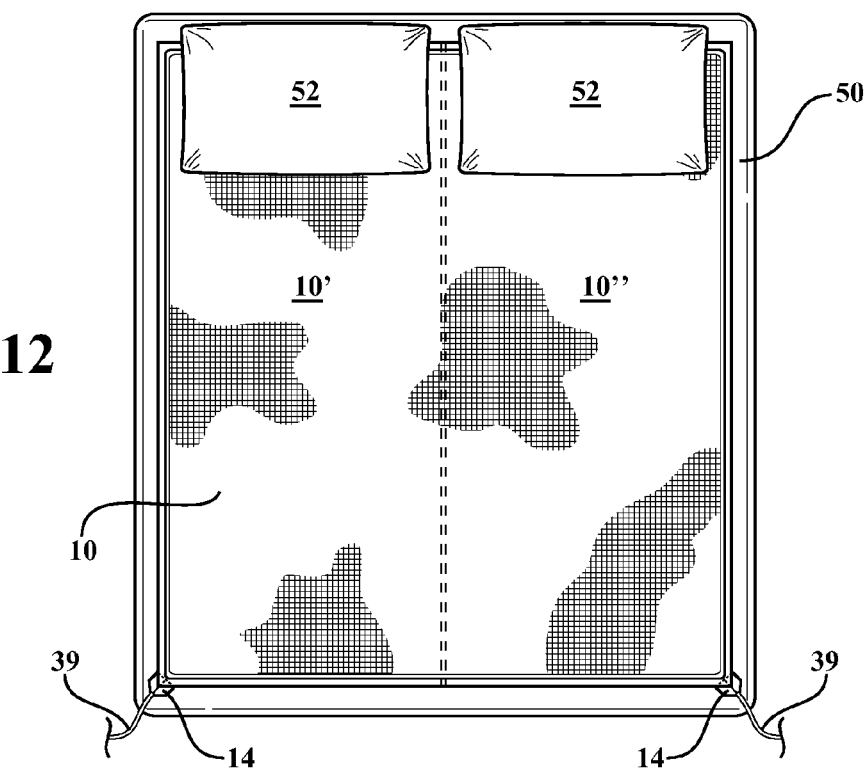
FIG. 12 is a plan view of another embodiment of an apparatus for measuring a subject at rest as disclosed herein.
Figure 13:
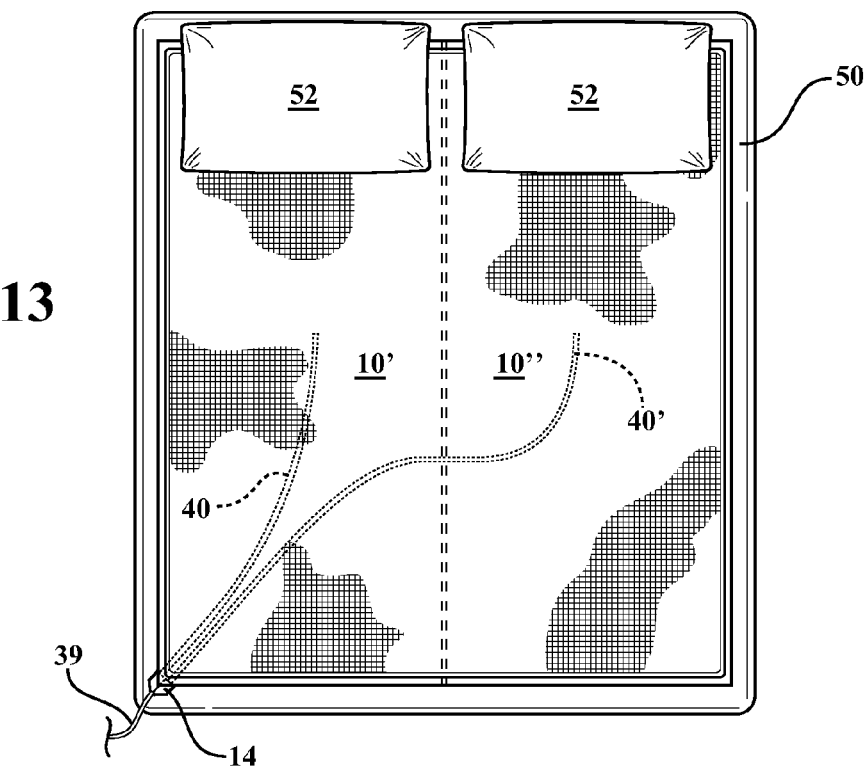
FIG. 13 is a plan view of another embodiment of an apparatus for measuring a subject at rest as disclosed herein.

The fluid bladder 10 can include multiple discrete compartments, with each compartment including a housing 14 with a pressure sensor module 15. For example, as illustrated in FIG. 11B, the bladder 10 of FIG. 11A can be formed into two discrete compartments such that the housing 14 in the upper compartment senses heart rate and respiration and the housing 14 in the lower compartment senses whether the subject is sitting up, for example. As illustrated in FIG. 12, if the substrate 50 is large enough for two subjects, the bladder 10 can include two discrete compartments 10', 10", each including its own housing 14 with pressure sensor module 15 for separately detecting the vital signs of the two subjects. However, the pressure detected by a single sensor 16 can indicate vital signs of multiple subjects. For example, each of the plurality of tubes 40 extending from the tubular aperture 30 of the housing 14 may terminate one in each compartment. This is illustrated in FIG. 13. The tube 40' can be hermetically sealed between the two compartments 10', 10".

Figure 14:
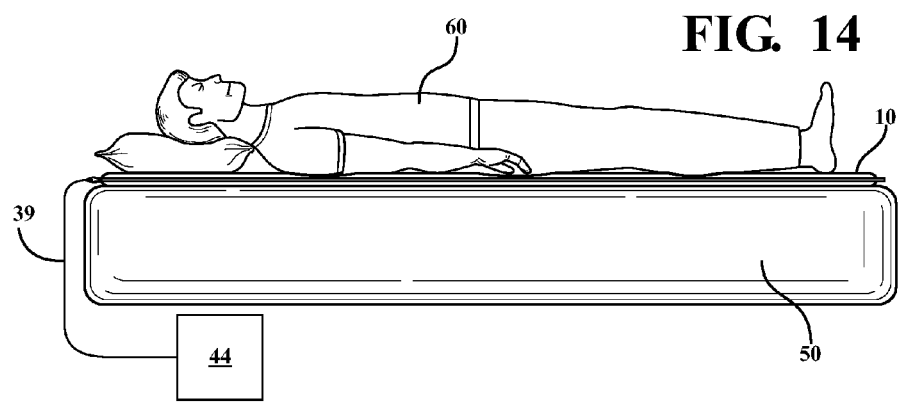
FIG. 14 is a side view of an embodiment of an apparatus for measuring a subject at rest in use with a subject.

In use, as shown in FIG. 14, the inflated bladder 10 is placed between the subject 60 and the substrate 50 such as a bed or crib mattress. When the subject 60 is lying on the bladder 10, each of the user's heart beats and breaths can create a force on the bladder 10 that is transmitted to the fluid. As a result of the force input to the bladder 10 from a heart beat or breath, a wave can propagate through the fluid and be detected by the pressure sensor 16. The PCB 18 of the pressure sensor module 15 can output an electrical pressure signal a to a controller 44, which can analyze the pressure signal α to determine a heart rate, respiration rate, and/or other vital signs of the subject on the mattress 10. While changes in the dynamic pressure in the bladder 10 are used to monitor cardiopulmonary health status data (i.e., vital signs), static pressure in the bladder 10 can be used to measure a subject's weight. In this manner, the bladder 10 can be used to provide weight data (e.g., over time), or to detect the presence or absence of the subject on the bladder 10. The controller 44 can also be configured to determine other characteristics of the subject based on the pressure signal α, such as blood pressure, tossing and turning movements, rolling movements, limb movements, or the identity of the subject.

The controller 44, which can include a memory and a CPU for executing a program stored on the memory, can be hard-wired to the sensor module 15, in wireless communication with the sensor module 15 using, e.g., a standard wireless protocol (IEEE 802.11, Bluetooth, etc.), or the controller 44 can communicate with the sensor module 15 in other ways known to those skilled in the art. The controller 44 can include a transmitter, a display screen, and controls. The transmitter can relay the status signal β to a database or other source. The transmitter can be a wireless transmitter operating using a standard wireless protocol (e.g., IEEE 802.11, RF, Bluetooth, or 3G), though the transmitter can alternatively be hardwired to the remote source using a phone line, Ethernet line, or other connection. As a result, the database can store sleep information produced as a result of the status signal β, and the subject can be alerted to sleep issues based on long-term sleep trends or provided with other communications regarding the subject's sleep (e.g., an alarm warning of apnea), fitness level, cardiovascular condition, or other health information.

The controls can be used, for example, to instruct the sensor module 15 and/or controller 44 to operate in a privacy mode in which data is not detected, retained, displayed, transmitted, and/or analyzed, or to communicate with the database to obtain sleep information (e.g., sleep trends, sleep scores from previous nights, sleeping tips). The database can alternatively or additionally be accessible using a computer, e.g., via the internet.

While the invention has been described in connection with what is presently considered to be the most practical example, it is to be understood that the invention is not to be limited to the disclosed example but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for monitoring a subject at rest comprising:
an inflatable bladder comprising a cavity containing a fluid and a hermetically sealed seam;
a housing hermetically sealed within the seam, the housing having a distal end with a distal aperture there through opened to the cavity, a proximal end with a proximal aperture there through opened to atmosphere, and an opening accessing a recess having a track provided in each side wall of the recess;
a pressure sensor having a sensing side exposed to the cavity of the inflatable bladder and a reference side exposed to ambient air within the recess of the housing; and
a printed circuit board coupled to the pressure sensor, wherein the pressure sensor is operable to detect a pressure change within the cavity due to a force exerted by a subject on the inflatable bladder,
wherein the pressure sensor and the printed circuit board are mounted on a planar base configured to slide within each track through the opening into the recess so that the pressure sensor and printed circuit board are fully within the recess.

2. The apparatus of claim 1, wherein the pressure sensor has a stem configured to fit within the distal aperture to expose the sensing side of the pressure sensor to the fluid within the cavity while sealing the recess from the fluid within the cavity.

3. The apparatus of claim 1, wherein the housing further comprises a plug inserted within the opening in the proximal end, the plug having a first aperture which provides the proximal aperture through which the reference side of the pressure sensor is exposed to ambient air and a second aperture through which an electrical conduit extends between the printed circuit board and an external controller.

4. The apparatus of claim 3, wherein the first and second apertures are sealed with a frangible cap configured for removal prior to use.

5. The apparatus of claim 3, wherein the controller is configured to determine at least one vital sign of a subject on the inflatable bladder based on a signal from the printed circuit board.

6. The apparatus of claim 5, wherein the at least one vital sign is one or more of a heart rate, a respiration rate, movement, weight and presence of the subject on the inflatable bladder.

7. The apparatus of claim 1, wherein the force exerted on the inflatable bladder originates from at least one of a heart rate and a respiration rate of the subject.

8. The apparatus of claim 1, wherein the housing further comprises a plurality of tubes extending from the distal aperture into the cavity, each of the plurality of tubes terminating in a different location within the cavity of the inflatable bladder.

9. The apparatus of claim 8, wherein the inflatable bladder comprises a plurality of compartments, each compartment having a cavity, wherein each of the plurality of tubes is in fluid communication with a different one of the plurality of compartments.

10. The apparatus of claim 1, further comprising one or more housings, wherein the one or more housings are hermetically sealed within the seam in different locations around a perimeter of the inflatable bladder.

11. The apparatus of claim 10, wherein the inflatable bladder comprises a plurality of compartments, each compartment having a cavity, wherein each of the one or more housings is positioned at a location around the perimeter so that each of the one or more housings is in fluid communication with a different one of the plurality of compartments.

12. The apparatus of claim 1, wherein the inflatable bladder comprises two plastic shells hermetically sealed.

13. The apparatus of claim 1, wherein the housing is further configured to communicate fluid to the cavity from a source external the inflatable bladder.

14. The apparatus of claim 1, wherein the housing is sized and configured to have a dimension equivalent to an inflation valve.

15. A pressure sensing device for use with an inflatable bladder, the device comprising:
a housing comprising a center portion having an opening accessing a recess having a track provided in each side wall of the recess, the housing configured to be welded in a seam of the inflatable bladder;
a pressure sensor having a sensing side configured to be exposed to the cavity of the inflatable bladder through a distal end of the housing and a reference side configured to be exposed to ambient air within the recess of the housing; and a printed circuit board located within the recess and coupled to the pressure sensor, wherein the pressure sensor is operable to detect a pressure change within the cavity due to a force exerted by a subject on the inflatable bladder, wherein the pressure sensor and the printed circuit board are mounted on a planar base configured to slide within each track through the opening into the recess so that the pressure sensor and printed circuit board are fully within the recess.

16. The device of claim 15, wherein the pressure sensor has a stem fit within a tubular aperture in the distal end of the housing through which the sensing side of the pressure sensor is configured for exposure to a fluid while sealing the recess of the housing from the fluid.

17. The device of claim 15, wherein the housing further comprises a plug configured to close the opening within the proximal end of the housing, the plug having a first aperture through which the reference side of the pressure sensor is exposed to ambient air and a second aperture sized to fit an electrical conduit between the printed circuit board and an external controller.

18. The device of claim 16, wherein the housing further comprises a plurality of tubes extending from the tubular aperture and configured to terminate at different locations within the cavity of the inflatable bladder.

* * * * *